United States Patent [19]
Meade

[11] Patent Number: 5,340,913
[45] Date of Patent: Aug. 23, 1994

[54] SYNTHESIS OF AROMATIC HETEROCYCLIC POLYMERS FROM A BIOSYNTHETICALLY PREPARED PRECURSOR

[75] Inventor: Thomas J. Meade, Altadena, Calif.

[73] Assignee: General Electric Company, Schenectady, N.Y.

[21] Appl. No.: 34,924

[22] Filed: Mar. 19, 1993

[51] Int. Cl.[5] .................. C08G 63/34; C08G 69/26
[52] U.S. Cl. ................................. 528/335; 528/339; 528/423; 528/424
[58] Field of Search ............... 528/335, 339, 423, 424

[56] References Cited

U.S. PATENT DOCUMENTS

| | | | |
|---|---|---|---|
| 3,038,005 | 6/1962 | McCormick et al. | 562/507 |
| 3,671,491 | 6/1972 | Loft et al. | 528/342 |
| 4,847,350 | 7/1989 | Harris | 528/179 |
| 5,030,706 | 7/1991 | Harris et al. | 528/183 |
| 5,091,500 | 2/1992 | Lysenko et al. | 528/226 |
| 5,151,490 | 9/1992 | Harris et al. | 528/185 |

*Primary Examiner*—Nathan M. Nutter
*Attorney, Agent, or Firm*—William H. Pittman

[57] ABSTRACT

2,4-Polybenzoxazoles are synthesized from a biosynthetically prepared AB monomer. The biosynthetically produced precursor, 2,3-dihydro-3-hydroxyanthranilic acid (DHAA), is chemically transformed to the AB monomer, 3-hydroxyanthranilic acid (HAA). This AB monomer is used to prepare said polybenzoxazoles.

6 Claims, No Drawings

SYNTHESIS OF AROMATIC HETEROCYCLIC POLYMERS FROM A BIOSYNTHETICALLY PREPARED PRECURSOR

FIELD OF THE INVENTION

This invention relates to the preparation of a novel set of homo- and copolymers containing the 2,4-polybenzoxazole unit prepared from the AB monomer 3-hydroxyanthranilic acid (HAA), which in turn is prepared from the biosynthetically produced 2,3-dihydro-3-hydroxyanthranilic acid (DHAA).

BACKGROUND OF THE INVENTION

Polybenzoxazoles may be formed by the condensation of a carboxylic acid (or its derivatives) with an o-aminophenol. The two sets of functional groups are referred to as A (indicating a carboxyl group affixed to a benzene ring) and B (indicating the amino and hydroxyl groups affixed to the same benzene ring), respectively. An AA monomer is a dicarboxylic acid, and BB and AB designations have corresponding meanings. Two examples of typical AB monomers are 3-amino-4-hydroxybenzoic acid and 4-amino-3-hydroxybenzoic acid.

Polybenzoxazoles are well known rigid polymers, environmentally resistant, and possessing high modulus and high strength properties. They have found utility in the preparation of thermally stable transparent coatings for solar cells that inhibit ionizing radiation, and in molecular composite technology where they are used as reinforcements in blends with other common polymers. However, the lack of an inexpensive process for preparing the AB monomer precursors has been a handicap to their manufacture.

U.S. Pat. No. 4,847,350 describes a rapid process for the formation of heterocyclic aromatic polymers by contacting multifunctional aromatic compounds, such as a diaminobenzenediol, a terephthaloyl halide and/or an aminohydroxybenzoic acid, with a sulfonic acid and a dehydrating agent. These are two-step reactions and result in the 2,5- and 2,6-polybenzoxazoles.

The AB monomer 3-amino-4-hydroxybenzoic acid is prepared from 4-hydroxybenzoic acid by nitration followed by reduction. The hydroxyl groups need not be protected. The AB monomer 3-nitro-4-hydroxybenzoic acid is reduced by aqueous stannous chloride in hydrochloric acid or by catalytic hydrogenation. Of these two possible aminohydroxybenzoic acids, the 3- amino-4-hydroxy isomer is more easily prepared because of ease of nitration.

By contrast, 3-hydroxyanthranilic acid (HAA), otherwise known as 2-amino-3-hydroxybenzoic acid, is a known compound that, so far as is known, has never been used in the preparation of polymers. HAA is a product of the transformation of the biosynthetically prepared DHAA and is the subject of this portion of the invention.

Various chemical syntheses of 2-amino-3-hydroxybenzoic acid have been reported. They are multistep processes and therefore extremely cost intensive.

Biosynthetically prepared monomers offer several advantages to traditional chemical preparations. These advantages include the use of cheap, renewable feedstocks, the capability of producing multifunctional products in a single step with unmatched chemical selectivity, and the effectiveness of synthesis under mild conditions.

The biosynthesis of DHAA was first reported in 1962 by McCormick et al., U.S. Pat. No. 3,038,005. It used a mutant strain of Streptomyces aureofaciens (Sa-652). The conversion of isolated and purified DHAA to anthranilic acid, m-hydroxybenzoic acid, HAA and hexahydro-3-hydroxyanthranilic acid were also outlined in the same report. However, the yield of DHAA by McCormick procedure has not been found reproducible.

In separate studies, DHAA was isolated from fermentation broth of Streptomyces zaomuceticus SF-1836 and was tested for antibacterial and antifungal activities; Betenandt, Liebigs Annalen der Chemi., 602, 61 (1957)]. The precise assignment of the structure of DHAA was later accomplished by Ganem et al., J. Am. Chem. Soc., 106, 2463 (1984), and independently by Walsh et al., J. Am. Chem. Soc., 106, 2443 (1984).

The present invention provides an improved process for producing relatively inexpensive DHAA. It further provides 2,4-polybenzoxazole homopolymers and copolymers made from AB monomer precursors including HAA.

SUMMARY OF THE INVENTION

In the process of this invention, HAA is polymerized to 2,4-polybenzoxazole homopolymers and copolymers. All these represent new classes of polymers.

In addition, DHAA is produced by inoculation of a broth containing carbohydrates, such as sucrose or starch, and a nitrogen source such as soybean meal, with mutant Streptomyces aureofaciens Sa-652 and allowing the biosynthesis of DHAA to take place under carefully controlled conditions of temperature, pH and oxygen supply. The DHAA is converted to HAA by dehydrogenation in the presence of a catalyst, typically palladium on carbon. Preferably, said dehydrogenation is effected in situ from the filtrate separated from the biomass.

DETAILED DESCRIPTION

All previous attempts to make polybenzoxazoles have been from chemical synthetic processes. This invention makes polybenzoxazoles from renewable feedstock nutrients, that is by a biochemical or biosynthetic route which is novel. The preferred process first produces DHAA which is then dehydrogenated to HAA, which in turn is polymerized to the new 2,4-polybenzoxazoles.

The 2,4-polybenzoxazoles of the present invention have structural units of the formula

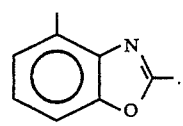

The positions of the three functional groups, i.e., the amine, hydroxy and carboxylic acid groups, in HAA dictate the 2,4-position of formula I, as opposed to the 2,5- or 2,6-positions.

Calculations based on molecular mechanics calculations indicate that the cis- and trans-2,4-polybenzoxazoles have dramatically different geometries than the previously known cis- and trans-2,5- and 2,6-polybenzoxazoles. Therefore, it is expected that the 2,4- polybenzoxazoles will exhibit new and unexpected properties.

Furthermore, since the process of the invention produces new 2,4-homopolymers, new 2,4-copolymers and 2,4-terpolymers as well as copolymers of the 2,4-2,5 and 2,4-2,6 varieties may also be produced by copolymerizing 2,3-AB monomers produced by this process with previously known 3,4-AB monomers.

A preferred technique according to the invention is the biosynthesis of DHAA from renewable feedstocks such as sucrose, cornstarch and soybeans exploiting a primary metabolic pathway of the organism. This biosynthesis and the subsequent chemical conversion of DHAA to HAA provide an example of a relatively low-cost route to a new monomer.

The DHAA is produced by aerobically fermenting an aqueous nutrient medium with a mutant strain of microorganisms of the species *Streptomyces aureofaciens*, designated Sa-652. It is a direct descendant of the chlorotetracycline-producing strain of *S. aureofaciens*, A-377, which was isolated from the soil, is described in U.S. Pat. No. 2,482,055 and is deposited at the Northern Regional Research Laboratories, Peoria, Ill., as NRRL 2209. Viable cultures of *Streptomyces aureofaciens* Sa-652 which produce the DHAA precursor were obtained from the American Type Culture Collection in Washington, D.C., where the strain has been assigned accession number ATCC 13,189.

The yield of DHAA in initial shake flask experiments was very low by comparison to published reports. Therefore, modifications to the culture, growth and fermentation parameters of *Streptomyces aureofaciens* Sa-652 organism and the compositions of the media were implemented to improve the yield and purity of DHAA.

The isolation of DHAA from fermentation broth may be accomplished in three steps.

(1) After filtration of the biomass, the filtrate is reduced to pH 1.5 with HCl, loaded onto a cation exchange column, washed with water and eluted with 1N $H_2SO_4$.

(2) The material is desalted, loaded onto a column of cellulose, eluted with 3:1:2 butanol:acetic acid:water, and the appropriate fractions pooled.

(3) The material is concentrated and recrystallized from acetic acid or methanol:water.

The UV/Vis spectra of DHAA exhibits a single featureless peak at 278 nm ($\epsilon$ 9110). The majority of impurities that are present may be estimated from the ratio of the peak height to base line at Abs 278 to the well to base line at Abs 235 when reading a total absorbance at Abs 278 of 1 in 0.1N HCl. Crystalline DHAA exhibits a 5:1 ratio. The 1H and 13 C NMR spectra are consistent with the proposed structure.

A mass spectrum of the material was obtained and the observed exact mass was 155.05810 (calculated value 155.05824). The fragmentation pattern of the compound is consistent with the proposed structure.

The aromatization of DHAA to HAA was carried out on samples of pure isolated DHAA and also in situ; i.e., without isolation of the DHAA from the fermentation broth. For the latter, the biomass and insoluble media components were filtered and the filtrate was reduced in volume by a factor of 5. A sheet of miracloth was placed over a 5 liter container, the contents of fermentation vessel were allowed to gravity filter, and the filtrate was placed in a 4 liter suction flask and filtered through a Gelman capsule filter (0.2 $\mu$m) under positive pressure. The filtrate was concentrated and placed in a 2 liter round-bottom flask equipped with a reflux condenser. Palladium on carbon catalyst (10%) was then added, and the reaction was followed by HPLC. At 80° C., the reaction was complete within 1 hour.

If corn steep liquor was used in the fermentation medium for the preparation of DHAA, the yield of HAA therefrom was consistently low (e.g., <20%). Presumably this is due to the high sulfur content of corn steep liquor which could poison the Pd/C catalyst. Substituting yeast extract, tryptose and tryptone for the corn steep liquor in the media provided in situ conversion yields of 60% based on the total absorbance of DHAA.

Polybenzoxazoles are normally prepared by thermal polymerization of acid or ester monomers in polymerization tubes or solution polymerization in polyphosphoric acid (PPA). The method developed by Wolf et al., known as the $P_2O_5$ adjustment method, was used for the synthesis of homo- and copolybenzoxazoles from HAA with minor modification. Polyphosphoric acid (PPA) of commercial grades proved inadequate for the preparation of high molecular weight polybenzoxazoles. PPA was therefore prepared fresh and used immediately. During the polymerization phase the PPA must activate the functional groups, maintain the solubility of the monomers and polymers and react with the water of condensation. A final narrow range of $P_2O_5$ content (>82-84%) is required to satisfy all these requirements and to provide a workable viscosity range for processing.

Using the outlined procedures above, a homopolymer was prepared and the TGA, DSC, IR and intrinsic viscosity measured. Due to the small catenation angle of 2,4-polybenzoxazoles, the reaction was carried out at slightly higher percent concentrations. The measured TGA inflection was 691° C. (17% loss). A similar procedure was followed for the preparation of copolymers from HAA.

Using the copolymer preparation outlined previously, 2,4-terpolymers can be prepared from HAA and monomers identified in U.S. Pat. No. 4,847,350.

A New Brunswick fermenter equipped with an internal dissolved oxygen and pH probe was used. Other fermenters commercially available may also be used.

The media and conditions for spore harvesting, vegetative growth media and conditions and fermentation media outlined in this invention are similar to those reported in the aforementioned U.S. Pat. No. 3,038,005. However, several critical modifications to the original biosynthetic procedure were implemented to increase yields of and purity of DHAA. They included alterations in the original medium composition and the parameters used for cell culture and growth. A primary concern to achieve overall efficiency of the synthesis of HAA was the elimination of the need to purify DHAA and proceed directly to the Pd catalyzed aromatization of DHAA after filtering the biomass and insoluble medium components. Therefore, media were developed that did not compromise the yield of DHAA but allowed for a facile conversion of DHAA to HAA.

The addition of a shear enhancing agent such as carboxymethylcellulose to the fermentation medium has facilitated the breakup of the filamentous mycelium that normally forms large mats upon growth of the bacteria. This biologically inert material provided an increase in the shear potential of the medium and prevented the mycellular mats from reaching a size that would inhibit the transport of oxygen. As a result, an increase of 2–3 g/l yield of DHAA was achieved. A yield of 8 g/l of DHAA is currently produced in 5-liter fermentation experiments.

The preferred growth of spores via Sa-652 was accomplished by using a 3 liter Fernbach flask with Difco's yeast malt extract agar at 27° C. under a blanket of sparged oxygen and a sterilized foam plug. Other means of obtaining suitable spores are less efficient. The preferred method of harvesting spores employs a 10% glycerol solution in sterilized water.

The preferred vegetative medium for spor growth, comprising sucrose, corn steep liquor and ammonium sulfate, is similar to that described by McCormick et al. U.S. Pat. No. 3,038,005. However, the calcium carbonate was eliminated from the recipe. Vegetative innoculum was grown from spores harvested as described above. The temperature for vegetative development was 28° C. Erlenmeyer flasks (500 ml) containing 100 ml of sterilized medium at pH 6.8 were inoculated with $2 \times 10^7$ spores. The medium consisted of 20 g/l of corn steep liquor, 30 g/l sucrose and 2 g/l ammonium sulfate. The pH was aseptically maintained at 6.8 during the entire course of growth.

The preferred fermentation medium for maximum production of DHAA comprises nutrients and mineral substances such as sucrose, corn steep liquor or solids, soybean meal, carboxymethylcellulose, ammonium sulfate, ammonium chloride, iron sulfate heptahydrate, manganese sulfate tetrahydrate, zinc sulfate heptahydrate and cobalt chloride hexahydrate. Sigma antifoam B was added on demand. The pH was maintained at the experimentally derived optimum of 6.8, however, a pH 6.5 to 7.1 was found suitable. If the pH was allowed to drop below 6, the production of DHAA was significantly reduced. The preferred temperature was 28° C., however, 25° C. to 37° C. and an agitator speed of 400 rpm (New Brunswick BioFlow III, 5 liter vessel) was sufficient to produce DHAA.

To avoid catalyst poisoning during the in situ conversion of DHAA to HAA, the corn steep liquor in the above fermentation medium may be replaced with a mixture of yeast extract, tryptose and tryptone. However, the resulting fermentation medium does not yield the highest amounts of DHAA, typically yielding only about 4 grams/liter. An alternative medium comprising sucrose, yeast extract, tryptose, tryptone, soybean meal, ammonium sulfate, ammonium chloride, iron sulfate heptahydrate, zinc sulfate heptahydrate, manganese sulfate tetrahydrate, cobalt chloride hexahydrate and carboxymethylcellulose typically yields about 6-8 grams/liter. Sigma antifoam B was added on demand. The pH was adjusted to 6.8, sterilized and aseptically readjusted to pH 6.8. The temperature of the fermenter was maintained at 28° C. and an agitator speed of 400 rpm was used.

The invention will be described in greater detail in conjunction with the following specific examples. Unless otherwise indicated, all parts and percentages are by weight.

EXAMPLE 1

Wheaton vessels (1000 ml) were prepared with a neoprene stopper with inlets for a pH probe, sparge tube and acid/base addition. The conditions employed were those of McCormick et al. modified as described hereinabove and with the employment of a fermentation medium which was a mixture of sucrose, 55 g/l; corn steep liquor, 20 g/l; soybean meal, 2.5 g/l; carboxymethylcellulose, 5 g/l; ammonium sulfate, 4 g/l; ammonium chloride, 1.5 g/l; iron sulfate, 0.04 g/l; manganese sulfate tetrahydrate, 0.05 g/l; zinc sulfate heptahydrate, 0.1 g/l; cobalt chloride hexahydrate 0.005; and Sigma antifoam B added on demand. There was also added 200 ml of a vegetative inoculum previously grown (36 hrs.) using 2 ml of harvested spores at a concentration of 100 million spores/ml. The pH of the medium was adjusted to 6.8 with 2N KOH and was internally regulated during the fermentation to 6.8 with 2N HCl or 2N KOH. While the vessel was stirred using a magnetic stirring bar, oxygen was sparged through the solution at a rate of 2 liters per minute.

The yield of DHAA produced as described above, as determined by ultraviolet spectroscopy, was about 4 g/l. In comparison, the yield in a shake flask was about 1.2 g/l.

EXAMPLE 2

Into a 5 liter New Brunswick Bioflow III fermenter were introduced 4 liters of the fermentation medium which contained no corn steep liquor and comprised sucrose, 55 g/l; yeast extract, 3 g/l; tryptose, 2 g/l; tryptone, 5 g/l; soybean meal, 2.5 g/l; carboxymethylcellulose, 5 g/l; ammonium sulfate , 4 g/l; ammonium chloride, 1.5 g/l; iron sulfate heptahydrate, 0.04 g/l; manganese sulfate tetrahydrate, 0.05 g/l; zinc sulfate heptahydrate, 0.1 g/l; cobalt chloride hexahydrate 0.005; and Sigma antifoam B added on demand. The vegetative inoculum and pH conditions were as described in Example 1. The temperature of the fermenter was maintained at 28° C. and an agitator speed of 400 rpm was used. Oxygen was sparged at a flow rate of 2–3 l/min. and monitored internally with a dissolved oxygen probe. The yield of DHAA was about 4 g/l.

EXAMPLE 3

The procedure of Example 2 was repeated using the fermentation medium of Example 1 to which 0.5 g/l carboxymethylcellulose had been added. The yield of DHAA was 6–8 g/l.

EXAMPLE 4

The isolation of DHAA from the fermentation broth was carried out by modifications of published procedures. The filtrate was passed through a column of cellulose after the cation exchange column prescribed and eluted with 3:1:2 butanol:acetic acid water. Microcrystalline DHAA was isolated after concentration of the eluant and characterized by 5:1 ratio of peak height-to-baseline at Abs 278 versus the well-to-baseline at Abs 235 nm and a UV absorbance maximum of 278 nm, NMR and mass spectrometry.

EXAMPLE 5

The volume of the filtrate from the fermentation broth (from Example 3) was reduced to about 1 liter by water evaporation. 25 grams of 10% of Pd/C catalyst was added and the mixture was heated and refluxed for 30 minutes, cooled, and the pH was adjusted to 2 with HCl, and the batch was filtered. The volume was reduced to 100–200 ml, and HAA was isolated by HPLC with 60–65% yield.

EXAMPLE 6

6.0 g. of 85.3% phosphoric acid was cooled to 0° C. on an ice bath. 9.72 g. of phosphorus pentoxide (88%) was added to the acid with stirring. The viscous mass was heated to 150° C., with stirring for 6 hours under nitrogen atmosphere and cooled. 2.6 grams of dried HAA was added to the viscous mass. The mixture was heated to 185° C. for an additional 18-28 hours. The resulting mixture was immersed in water to precipitate the homopolymer, which was filtered and washed with water for 24 hours in a Soxhlet extractor. The washed 2,4-homopolybenzoxazole was vacuum dried at 100° C. for 24 hours. It was characterized by infrared spectroscopy (IR), thermogravimetric analysis (TGA) and differential scanning calorimetry (DSC), and the intrinsic viscosity was measured. IR analysis revealed the characteristic bands for polybenzoxazole and the appropriate substitution pattern on the ring. TGA revealed an inflection at 691° C. with a total weight loss of 17%.

EXAMPLE 7

Into a 100-ml three neck flask equipped with a mechanical stirrer, nitrogen outlet, and oil bubbler was placed 6.0 g of 85.3% $H_3PO_4$ that was cooled to 0° C. in an ice bath. To this solution was added 9.72 g of $P_2O_5$ (88% $P_2O_5$ content) with stirring. The viscous mass was heated to 150° C. and allowed to stir for 6 hours; then 1.7 g of HAA (2.1 mmol) and 1.7 g of 3-amino-4-hydroxybenzoic acid (2.1 mmol) which were previously dried in vacuo were added. The temperature was raised to 185° C. and the reaction allowed to proceed for an additional 18-32 hours under positive nitrogen pressure. The resulting reaction mixture was precipitated in water, filtered and washed with water for 24 hours in a Soxhlet extractor. The solid was placed in a vacuum oven and dried at 100° C. for 24 hours and the product was characterized by IR, TGA and DSC and the intrinsic viscosity of the material was measured.

EXAMPLE 8

The procedure of Example 7 was repeated, but 4-amino-3-hydroxybenzoic acid was substituted for the 3-amino-4-hydroxybenzoic acid.

EXAMPLE 9

The procedure of Example 7 was repeated, but 2,3-diaminobenzoic acid was substituted for the 3-amino-4-hydroxybenzoic acid.

The copolymer that possessed the highest measured TGA was composed of HAA and 3-amino-4-hydroxybenzoic acid, which had an inflection at 744° C. with a 16% weight loss.

What is claimed is:

1. A novel 2,4-polybenzoxazole having repeating units of the formula

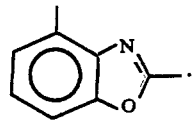

2. A 2,4-polybenzoxazole according to claim 1 which is a homopolymer.

3. A 2,4-polybenzoxazole according to claim 1 which is a copolymer.

4. A copolymer according to claim 3 wherein the comonomer is 3-amino-4-hydroxybenzoic acid.

5. A copolymer according to claim 3 wherein the comonomer is 4-amino-3-hydroxybenzoic acid.

6. A copolymer according to claim 3 wherein the comonomer is 2,3-diaminobenzoic acid.

* * * * *